United States Patent [19]

Banno et al.

[11] 4,448,752
[45] May 15, 1984

[54] LIQUID DISTRIBUTING DEVICE FOR USE IN CHEMICAL ANALYZER

[75] Inventors: Taiichi Banno; Ryo Fujimori, both of Hachioji; Hiroshi Takekawa, Sagamihara; Kazuo Hijikata, Hachioji, all of Japan

[73] Assignee: Olympus Optical Co., Ltd., Japan

[21] Appl. No.: 330,449

[22] Filed: Dec. 14, 1981

[30] Foreign Application Priority Data

Dec. 12, 1980 [JP] Japan .................................. 55-175490

[51] Int. Cl.³ .......................... G01N 1/14; G01N 35/08
[52] U.S. Cl. .................................... 422/81; 73/864.21; 422/100
[58] Field of Search ........................... 422/63, 81, 100; 73/864.21, 864.81

[56] References Cited

U.S. PATENT DOCUMENTS

| | | | |
|---|---|---|---|
| 4,108,608 | 8/1978 | Maher et al. | 422/100 |
| 4,117,727 | 10/1978 | Friswell et al. | 73/864.21 |
| 4,130,394 | 12/1978 | Negersmith | 422/100 |
| 4,162,689 | 7/1979 | Zarodowski | 422/100 |
| 4,318,885 | 3/1982 | Suzuki et al. | 422/63 |
| 4,341,736 | 7/1982 | Drbal et al. | 422/100 |
| 4,345,483 | 8/1982 | Paletta et al. | 422/100 |
| 4,351,799 | 9/1982 | Gross et al. | 422/63 |

FOREIGN PATENT DOCUMENTS 104382  8/1979  Japan .............................. 73/864.81

Primary Examiner—Bradley Garris
Attorney, Agent, or Firm—Parkhurst & Oliff

[57] ABSTRACT

In a distributing device for sucking a desired amount of a sample liquid in a sample vessel and discharging the thus sucked sample liquid into a reaction vessel, a probe for sucking and discharging the liquid is connected to a syringe driven by a pulse motor. A photoelectric detector is provided for detecting whether the sample liquid is present or not up to a predetermined level in the sample vessel and an actual amount of the sample liquid aspirated by the syringe is detected by a counter which counts clock pulses during the aspirating operation. When the liquid level descends lower than the predetermined level, the counting operation is stopped. The actual amount of the aspirated liquid in the probe is compared with a desired amount stored in a memory. When the actual amount of the sucked liquid is smaller than the desired value, an alarm is produced.

18 Claims, 3 Drawing Figures

LIQUID DISTRIBUTING DEVICE FOR USE IN CHEMICAL ANALYZER

BACKGROUND OF THE INVENTION

This invention relates to a liquid distributing device for use in an automatic analyzing apparatus, for delivering a given amount of a liquid such as a sample liquid from a sample cup into a reaction vessel comprising a probe to be immersed into the sample liqid contained in the sample cup, pumping means such as a syringe connected to said probe for sucking and discharging a given amount of the sample liquid through said probe and means for driving said syringe.

In automatic analyzing apparatuses, various distributing devices are used to deliver various kinds of liquid such as samples, reagents and diluents by means of one probe. Such distributing devices perform a sucking operation even if a liquid level of the liquid contained in a vessel descends below a tip of a probe and thus air is sucked in the probe. Therefore, the amount of the liquid sucked in the probe is smaller than a given amount to be delivered. This results in that the predetermined amount of the liquid could not be delivered and erroneous measurement might be introduced. In order to avoid the above mentioned drawback, it has been proposed to detect a liquid level of the liquid during the aspiration. This can be effected by providing a photoelectric detecting means having an elongated detecting region extending in an axial direction of the vessel, because the liquid level descends in accordance with the aspiration. Therefore, the photoelectric detecting means is liable to be large in size and complicated in construction. It has also been proposed to descend the probe in accordance with the progress of aspiration. However, in such a case, a very complicated probe driving mechanism must be provided.

SUMMARY OF THE INVENTION

The present invention has for its object to provide a novel and useful distributing device which can obviate the above mentioned delivery error causing an erroneous measurement by means of a simple construction.

To fulfill the object, the present invention provides a distributing device for delivering a given amount of a liquid from a first vessel into a second vessel comprising a probe to be immersed into the liquid contained in the first vessel, pumping means connected to said probe for sucking and discharging a given amount of the liquid through said probe and means for driving said pumping means, the improvement comprises means for detecting whether or not the liquid is present in the first vessel up to a predetermined level to produce a liquid detection signal;

means for receiving said liquid detection signal to produce a first signal representing an actual amount of the liquid sucked through the probe;

means for storing a second signal representing said given amount of liquid to be delivered; and means for comparing said first and second signals with each other to produce a discrimination signal denoting that the actual amount of the sucked liquid is not equal to the given amount to be delivered into the second vessel.

DESCRIPTION OF THE PREFERRED EMBODIMENTS

Figure 1:
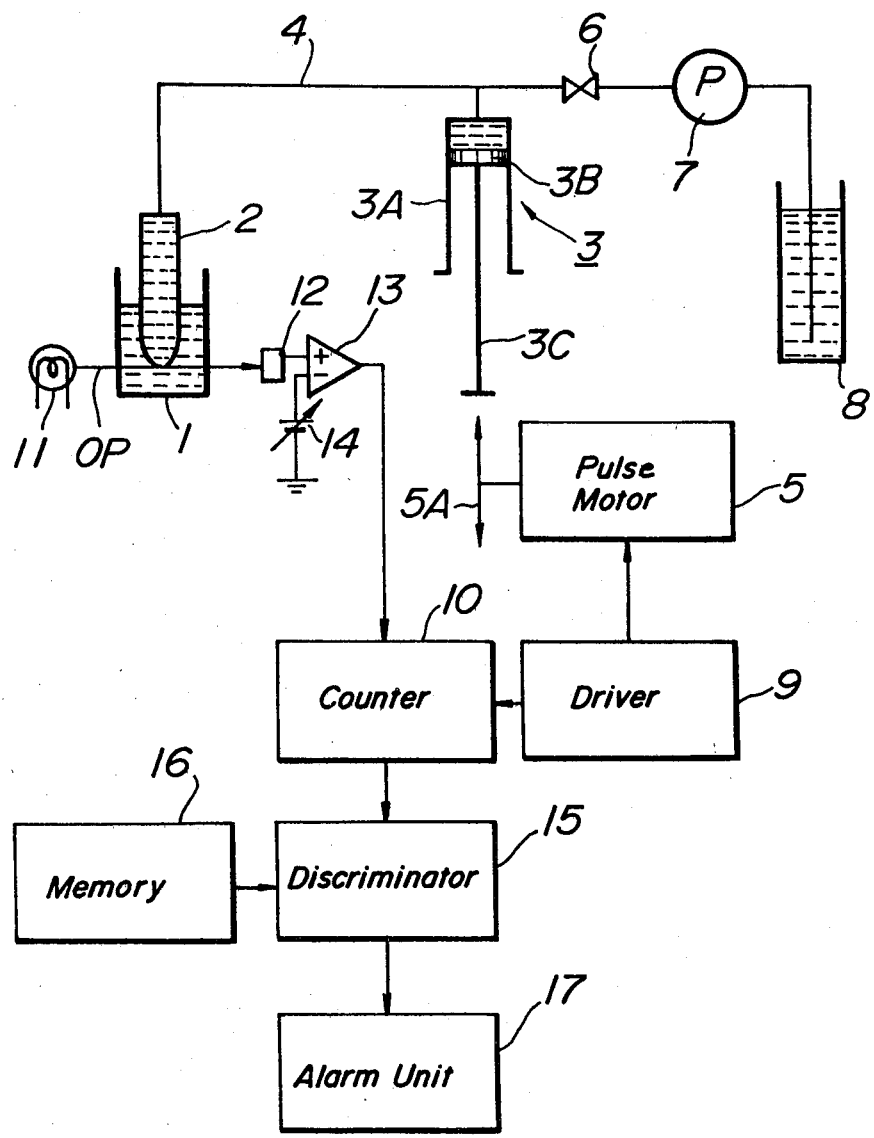
FIG. 1 is a schematic diagram showing one embodiment of the distributing device according to the invention.

In FIG. 1, a sample vessel 1 for containing a sample solution is mounted on, for instance, a turntable of a sampler of an automatic analyzing apparatus (not shown). A probe 2 is arranged movably in vertical and horizontal directions and is first immersed in the sample solution to suck the sample. Then the probe 2 is moved upwards and is fed horizontally into a position above a reaction vessel (not shown). Then the sucked sample solution is discharged into the reaction vessel. This probe 2 is connected to a syringe 3 by means of a connecting tube 4. The syringe 3 operates as pumping means for sucking and discharging the sample and comprises a cylinder 3A, a piston 3B movably arranged inside the cylinder and a rod 3C having one end connected to the piston and the other end coupled to a pulse motor 5 by means of a suitable link mechanism 5A. By rotating the pulse motor 5, the rod 3C and thus the piston 3B are moved up and down. The syringe 3 is further connected to a washing liquid vessel 8 through a valve 6 and a washing pump 7 so as to discharge a washing liquid through the probe 2 to wash the probe. To the pulse motor 5 are supplied a given number of driving pulses from a driver 9 under control of a controlling circuit such as a microcomputer. The number of pulses supplied from the driver 9 to the pulse motor 5 are counted by a counter 10. A light source 11 and a light detector 12 are arranged at opposite positions with respect to the sample vessel 1. They are so arranged that an optical axis OP is set slightly lower than a tip position of the probe 2 when the probe 2 is immersed in the liquid to suck the liquid in the sample vessel 1. Then, a light emitted from the light source 11 is transmitted through the liquid in the sample vessel 1 and is received by the light detector 12. The light detector 12 is connected to one input of a comparator 13 having the other input connected to a variable voltage source 14. When an output from the light detector 12 becomes larger than a reference voltage produced by the variable voltage source 14 due to the fact that a liquid level descends lower than the optical axis OP, a count stop signal is supplied from the comparator 13 to the counter 10 so as to stop counting the driving pulses from the driver 9. The counter 10 is connected to a discriminator 15 to supply a count value to the discriminator 15. It should be noted that the count value represents an actual amount of the liquid 1 sucked through the probe 2. Moreover, a memory 16 is connected to the discriminator 15. The number of driving pulses necessary for sucking the given amount of the liquid to be delivered has been stored in the memory 16 by means of the controlling circuit. The number thus stored in this memory 16 is supplied to the discriminator 15. In the discriminator 15, the count value from the counter 10 is compared with the desired value stored in the memory 16. If the count value is smaller than the desired number, the discriminator 15 supplies a signal to an alarm unit 17 so as to activate an alarm.

Hereinafter, an operation of the distributing device according to the invention will be further explained. When the driving pulses are supplied from the driver 9 to the pulse motor 5 by means of the controlling circuit, the rod 3C is moved downward so that the sample solution in the sample vessel 1 is sucked into the probe 2. For the time being, it should be noted that the valve 6 is closed. After sucking a predetermined amount of the sample solution, the probe 2 is moved above the reaction vessel and the pulse motor 5 is driven again to deliver the sample solution into the reaction vessel. Next, the probe 2 is moved to a washing position (not shown) so as to discharge the washing liquid from the washing liquid vessel 8 by means of the washing pump 7 through the valve 6, which is now opened, and the probe 2, so that the syringe 3, the probe 2, and the connecting tube 4 are washed.

When the liquid level of the sample solution in the sample vessel 1 is still located above the optical axis OP near the tip of the probe 2 after the aspiration, all of the driving pulses supplied to the motor 5 for aspiration are counted by the counter 10, because the count stop signal is not supplied from the comparator 13 to the counter 10. In this case, since the count value of the counter 10 is the same as the desired value stored in the memory 16 so that an alarm is not activated. Contrary to this, when the liquid level of the sample solution drops below the optical axis OP during the aspiration, the subsequent driving pulses supplied from the driver 9 to the pulse motor 5 are not counted by the counter 10, because the comparator 13 supplies the count stop signal to the counter 10 during the aspiration. Therefore, the count value of the counter 10 becomes smaller than the desired value stored in the memory 16 and a signal is supplied from the discriminator 15 to the alarm unit 17 so as to raise an alarm.

As mentioned above, according to the invention the alarm is produced before discharging the sucked liquid. Whenever the aspirated amount is smaller than the predetermined amount, any erroneous measurement can be effectively prevented and abnormal analysis results can be identified by alarm marks on analysis reports. Moreover, in case of delivering the sample solution sucked at one time into a plurality of reaction vessels by means of the probe 2, if a required amount of the sample solution is not sucked, the amount of the sample solution which is sucked in the syringe 3 can be determined from the count value of the counter 10. Therefore, by previously providing a priority for test items, it is possible to deliver selectively the sample solution into reaction vessels from the beginning from the one of highest priority and to give the alarm only for items wherein the distribution cannot be performed. In such a case, it is also possible to cancel the sample delivering operation for the test items for which the given amounts of sample could not be delivered under control of the controlling circuit.

Furthermore, in regard to the means for detecting the liquid level of the sample solution, various known systems such as systems for measuring an electric resistance between electrodes, a reflection of light or ultrasonic wave, or an electrostatic capacity between an electrode and a liquid surface may be utilized instead of the photoelectric measuring system mentioned above.

Figure 2:
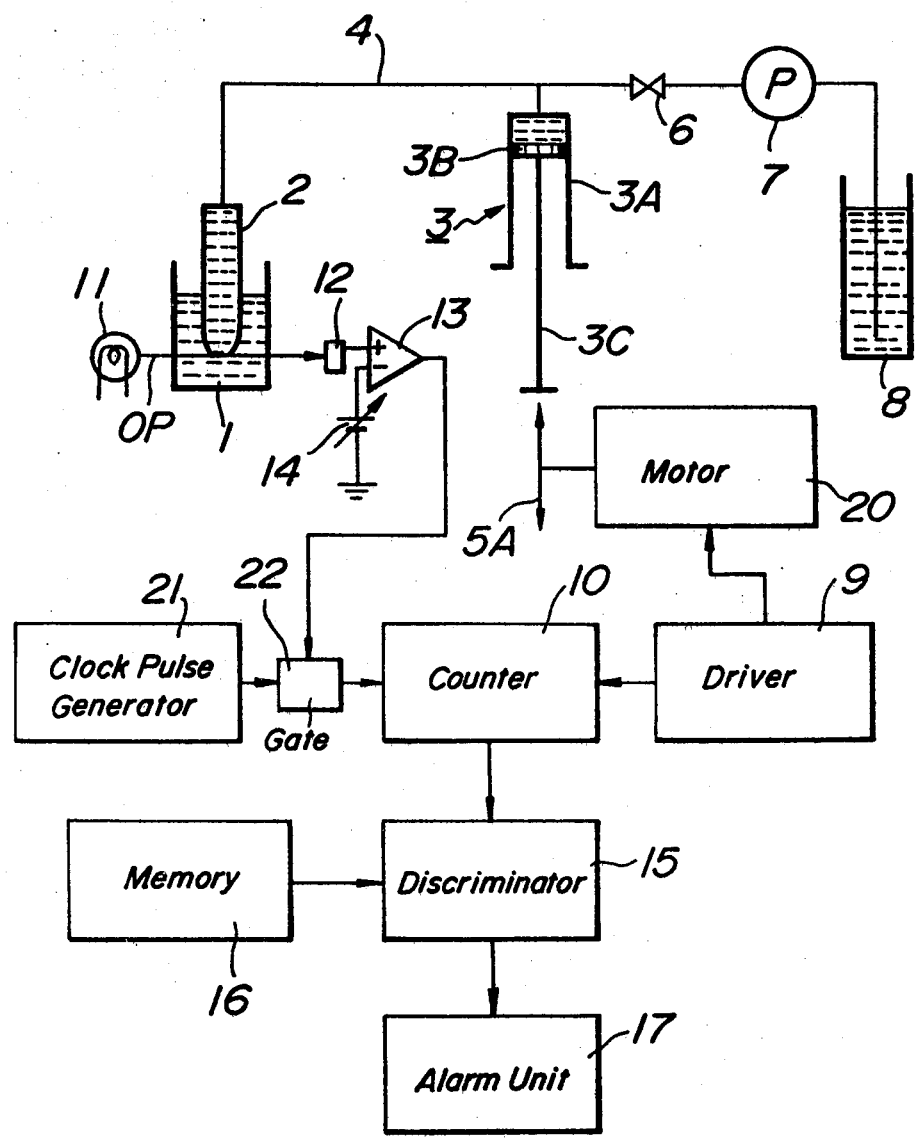
FIG. 2 is a schematic diagram illustrating another embodiment of the distributing device according to the invention.

FIG. 2 is a schematic diagram illustrating another embodiment of the distributing device according to the invention. For the sake of simplicity, the same numerals are used for denoting the same portions as those in FIG. 1. In this embodiment, a general AC or DC motor 20 is used for driving the syringe 3 instead of the pulse motor 5. Therefore, a driving electric current is supplied to the motor 20 for a time interval during which the predetermined amount of the sample solution can be sucked under the control of the controlling circuit (not shown). Further, in this embodiment, a clock pulse generator 21 is connected to the counter 10 through a gate 22, and also an output of the comparator 13 is supplied to the gate 22. The gate 22 is made OFF when the count stop signal is supplied from the comparator 13, and made ON when a signal is not supplied. The clock pulse generator 21 generates the pulses continuously which are counted by the counter 10 only for a time interval when the driving electric current is supplied from the driver 9 to the motor 20. Furthermore, in the memory 16 is stored a desired count value which is equal to the number of pulses generated from the clock pulse generator 21 for a time interval during which the driving electric current is supplied to the motor 20 for aspirating the predetermined amount of the liquid.

In this embodiment, as is the same as the aforementioned embodiment, when the liquid level of the sample solution in the sample vessel 1 does not descend to the optical axis OP of the photoelectric detector 11, 12, the count stop signal is not supplied from the comparator 13 to the gate 22. Therefore, the gate 22 is made ON and the count value of the counter 10 becomes the same as the desired value stored in the memory 16 so that the alarm unit 17 does not produce an alarm. Contrary to this when the liquid level of the sample solution descends below the optical axis OP during the aspiration the count stop signal is generated so as to make the gate 22 OFF. Therefore, the count value of the counter 10 becomes smaller than the desired value in the memory 16 and the discriminator 15 sends to the alarm unit 17 an alarm signal indicating that the given amount of sample has not been sucked.

Figure 3:
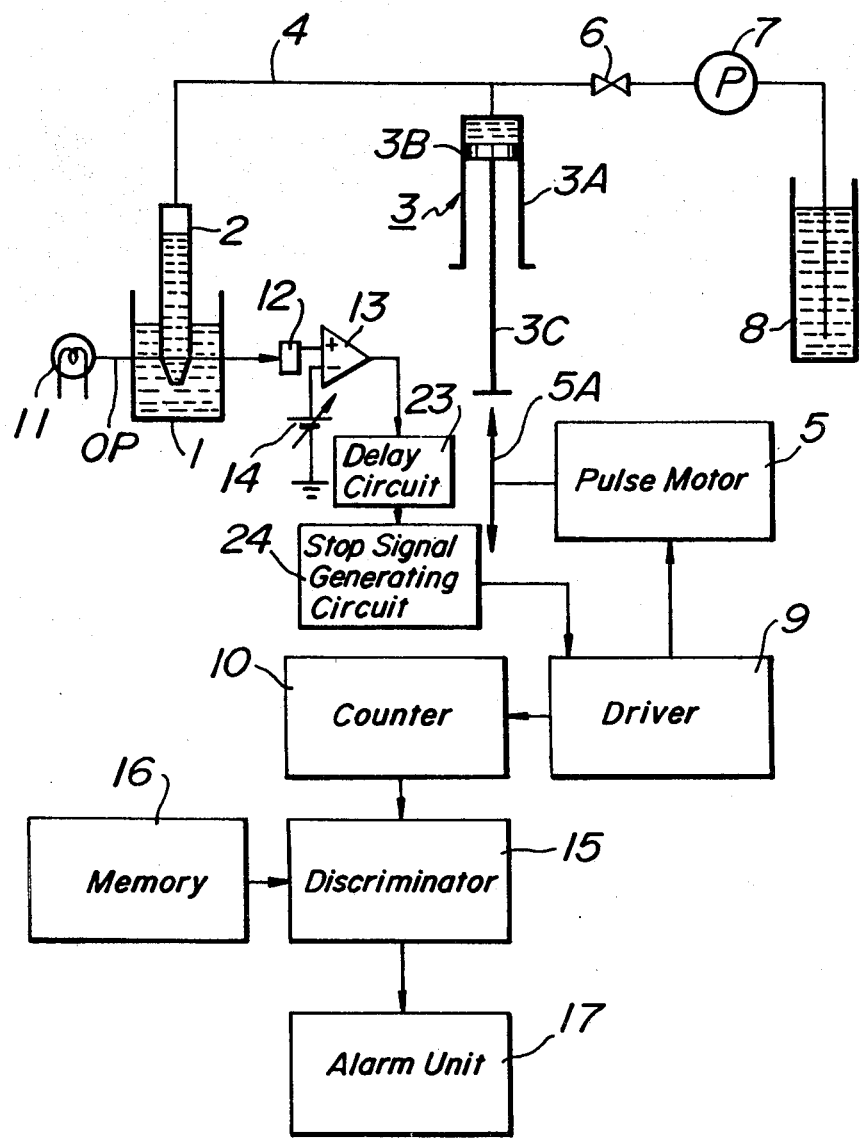
FIG. 3 is a schematic diagram depicting still another embodiment of the distributing device according to the invention.

FIG. 3 is a schematic diagram depicting still another embodiment of the distributing device according to the invention. In this embodiment, the optical axis OP of the photometric device 11, 12 is located slightly above the tip position of the probe 2 so as to prevent the syringe 3 from sucking air when the liquid level of the sample solution becomes below the tip position of the probe 2. Then, after detecting the liquid level of the sample solution at this optical axis OP, the sucking operation is carried out by the syringe 3 for a given short time interval until the surface of the sample solution reaches near the tip position of the probe 2 and after that the sucking operation of the syringe is stopped. To this end, in this embodiment, the signal generated from the comparator 13 is supplied to a stop signal generating circuit 24 through a delay circuit 23. After that, the stop signal generating circuit 24 supplies a stop signal to the driver 9 so as to stop supply of the driving pulse from the driver 9 to the pulse motor 5 and at the same time the counter 10 stops its counting operation.

In this embodiment, in case of sucking the sample solution utilizing the syringe 3, if the surface of the sample solution does not reach the optical axis OP, the alarm unit 17 does not operate as it operated in the previous embodiments. On the contrary, when the surface of the sample solution reaches the optical axis OP, the signal is supplied from the comparator 13 to the delay circuit 23 and after the given time the delay circuit 23 supplies the signal to the stop signal generating circuit 24. During this delay time the sample solution existing between the optical axis OP and the tip position of the probe 2 is sucked by the syringe 3. Then, the stop signal generating circuit 24 supplies the stop signal to the driver 9 so as to stop the supply of the driving pulse to the pulse motor 5, so that a driving of the pulse motor 5 and a sucking of the syringe 3 are ceased. Moreover, since the supply of the driving pulse from the driver 9 to the pulse motor 5 is stopped, the count value of the counter 10 is not same as the stored value of the memory 16 so that the signal is supplied to the alarm unit 17 to raise an alarm.

In the embodiment shown in FIG. 3, it is possible to stop the aspirating operation of the syringe 3 before the liquid level of the sample solution becomes a threshold level at which point the aspiration could not be effected and then an alarm is produced by the alarm unit 17. Moreover, the distributing device illustrated in FIG. 3 is formed by modifying the embodiment shown in FIG. 1. It is possible to apply such a modification to the embodiment shown in FIG. 2. Furthermore, in the embodiment shown in FIG. 3, it is necessary to set up the photometric position defined by the optical axis OP at such a position that an amount of the sample solution between the tip position of the probe and the photometric position does not exceed a total amount of sample solution to be sucked by the syringe 3.

By the distributing device according to the invention, it is possible to prevent an erroneous measurement due to inaccurate delivery of the liquid such as the sample, reagent and diluent even if the amount of the liquid is smaller than necessary.

The present invention is not limited to the embodiments mentioned above, but many modifications may be conceived within the scope of the invention. For example, in the embodiments mentioned above, a detection of the sample shortage is carried out by comparing the count value of the pulses with the predetermined value, but it is possible to compare them in an analogue manner. For instance, an amount of electric charge stored in a capacitor during the aspiration time may be compared with a predetermined voltage.

What is claimed is:

1. A distributing device for delivering a given amount of liquid from a first vessel into a second vessel, comprising:
   a probe, said probe having a tip and being selectively immersed in said first vessel for removing said given amount of liquid therefrom;
   pumping means connected to said probe for aspirating and discharging said given amount of liquid through said probe;
   means for driving said pumping means;
   means for detecting an amount of liquid remaining in said first vessel and producing a liquid detection signal when said amount of liquid remaining in said first vessel is at a predetermined level corresponding to the proximity of the tip of the probe when immersed in said first vessel;
   means for receiving said liquid detection signal to produce a first signal representative of an actual amount of liquid aspirated through the probe;
   means for storing a second signal representing said given amount of liquid to be delivered; and
   means for comparing said first and second signals with each other to produce a discrimination signal denoting that the actual amount of the aspirated liquid is not equal to the given amount to be delivered into the second vessel.

2. A device according to claim 1, wherein said first signal producing means comprises a counter which counts pulses for a time period during which said means for driving is operated to effect the liquid aspiration and is disabled upon receiving the liquid detection signal.

3. A device according to claim 2, wherein said first signal producing means further comprises a clock pulse generator for producing said pulses to be counted by the counter and a gate connected between the clock pulse generator and the counter and said gate is closed upon receipt of said liquid detection signal.

4. A device according to claim 2, wherein said pulses to be counted by the counter are supplied from the driving means.

5. A device according to claim 4, wherein said driving means comprises a pulse motor and a driver for supplying driving pulses to said pulse motor and said pulses to be counted by the counter are related to said driving pulses.

6. A device according to claim 1, wherein said means for detecting the liquid level comprises a light source emitting a light beam, a light detector for receiving the light beam transmitted through the first vessel and a comparator for comparing an output signal from the light detector with a predetermined reference value, said light source and light detector having an optical axis situated at said predetermined level.

7. A device according to claim 1, wherein said predetermined level is set slightly above a tip of the probe which has been immersed in the liquid.

8. A device according to claim 7, further comprising means for stopping the operation of the driving means when said liquid detection signal is produced.

9. A device according to claim 8, wherein said stopping means comprises a delay circuit for delaying the liquid detection signal and a stop signal generator for producing a stop signal in response to a delayed liquid detection signal.

10. A device according to claim 1, wherein said pumping means comprises a syringe having a cylinder connected to the probe, a piston slidably arranged inside the cylinder and a rod having one end connected to said piston and the other end coupled to the driving means.

11. A device according to claim 1, further comprising means for producing an alarm signal in response to said discrimination signal.

12. A device for distributing a preselected amount of liquid comprising:
   means for pumping liquid comprising motor means and driver means for powering said pumping means, said driver means operating to produce a driving signal indicative of the operation of said driver means;
   intake means for receiving liquid from a first vessel for delivery to said pumping means, said intake means having an inlet opening;
   discharge means for discharging liquid into a second vessel;
   means for detecting the presence or absence of liquid remaining in the first vessel in the proximity of said inlet opening, said detecting means operating to produce a detection signal indicative of whether liquid is present or absent;

means for receiving said liquid detection signal and said driving signal so as to produce a first signal representing an actual amount of the liquid pumped into said intake means by said pumping means;

means for storing a second signal representing said preselected amount of liquid to be delivered, said storing means operating to generate said second signal;

means for comparing said first and second signals to produce a discrimination signal indicative of whether or not the actual amount of liquid pumped into said intake means is substantially equal to the preselected amount;

whereby a first signal derived from the signal outputs of said driver means and said detecting means is compared with a second signal representative of the preselected amount to determine whether the preselected amount was actually pumped from a first vessel to a second vessel.

13. The device of claim 12, further comprising a clock pulse generator for generating clock pulses and gate means for gating the clock pulses in accordance with the duration of said detection signal, said gate means having an input operatively connected to said detecting means and an output operatively connected to said receiving means so that the detection signal enters said receiving means in the form of clock pulses, said receiving means comprising counter means for counting said clock pulses.

14. A device for distributing a preselected amount of liquid comprising:

means for pumping liquid comprising motor means and driver means for powering said pumping means;

intake means for receiving liquid from a first vessel for delivery to said pumping means, said intake means having an inlet opening;

discharge means for discharging liquid into a second vessel;

means for detecting the presence or absence of liquid remaining in the first vessel in the proximity of said inlet opening, said detecting means operating to produce a detection signal indicative of whether liquid is present or absent;

means for producing a stop signal, said detection signal being received by said stop signal producing means such that said stop signal is produced when said detection signal indicates that an absence of liquid is detected by said detecting means, said driver means being electrically connected to said stop signal producing means such that said driver means is stopped by a stop signal;

receiving means electrically connected to said driver means and responsive to the operation of said driver means, said receiving means operating to produce a first signal indicative of whether or not said driver means is operating;

means for storing a second signal representing said preselected amount of liquid to be delivered, said storing means being operative to generate a second signal; and means for comparing said first and second signals electrically connected to said receiving means and said storing means, said comparing means operating to produce a discrimination signal for indicating whether or not the actual amount of liquid pumped into said intake means is substantially equal to said preselected amount;

whereby the first and second signals may be compared by said comparing means and a determination can readily be made from the output of the comparing means as to whether the preselected amount of liquid was delivered by said pumping means from a first vessel into a second vessel.

15. The device of claim 12, 13, or 14 wherein said pumping means comprises a syringe having a cylinder and a piston movably arranged inside said cylinder, said piston being driven by said motor means which is responsive to driving pulses from said driver means.

16. The device of claim 12, 13 or 14 wherein said detecting means comprises a light detector and a comparator, said light detector operating to detect light and emit an electrical signal dependent upon the amount of light detected into said comparator, said comparator operating to compare said electrical signal with a reference voltage to thereby emit a detection signal indicative of the presence or absence of liquid.

17. The device of claim 14 further including delay means for delaying the detection signal, said detecting means being positioned to detect the level of liquid above said inlet opening and said delay means operating to delay said detection signal by an amount of time required to pump the amount of liquid existing between the level at which said detecting means is positioned and the level of said inlet opening.

18. The device of claim 12 or 14 further comprising alarm means for producing an alarm signal electrically connected to said comparing means and responsive thereto.

* * * * *